United States Patent [19]

Schuler

[11] Patent Number: 5,547,602

[45] Date of Patent: Aug. 20, 1996

US005547602A

[54] MOISTURIZING SOAP BAR

[75] Inventor: William H. Schuler, Edgewood, Ky.

[73] Assignee: The Broxon Marketing Group, Inc., Chicago, Ill.

[21] Appl. No.: 439,855

[22] Filed: May 12, 1995

[51] Int. Cl.$^6$ .................... C11D 9/00; C11D 9/30
[52] U.S. Cl. ............ 510/152; 510/154; 510/156; 510/151; 510/484
[58] Field of Search .................. 252/108, 122, 252/132, 174.17, DIG. 16, 134, 174.21, 544, 550

[56] References Cited

U.S. PATENT DOCUMENTS

| | | | |
|---|---|---|---|
| 3,829,563 | 8/1974 | Barry et al. | 424/70 |
| 3,959,491 | 5/1976 | Young et al. | 424/359 |
| 4,537,782 | 8/1985 | Millet et al. | 514/774 |
| 4,704,224 | 11/1987 | Saud | 252/132 |
| 4,941,990 | 7/1990 | McLaughlin | 252/121 |
| 4,976,953 | 12/1990 | Orr et al. | 424/47 |
| 5,002,680 | 3/1991 | Schmidt et al. | 252/90 |
| 5,076,953 | 12/1991 | Jordan et al. | 252/108 |
| 5,096,608 | 3/1992 | Small et al. | 252/132 |
| 5,154,849 | 10/1992 | Visscher et al. | 252/174.15 |
| 5,204,014 | 4/1993 | Redd et al. | 252/117 |
| 5,219,487 | 6/1993 | Heile, Jr. et al. | 252/108 |
| 5,262,079 | 11/1993 | Kacher et al. | 252/112 |
| 5,312,559 | 5/1994 | Kacher et al. | 252/125 |
| 5,328,632 | 7/1994 | Redd et al. | 252/174 |
| 5,389,279 | 2/1995 | Au et al. | 252/108 |

FOREIGN PATENT DOCUMENTS

| | | | |
|---|---|---|---|
| 62-36304 | 2/1987 | Japan . | |
| 63-145400 | 6/1988 | Japan | 252/132 |
| 0145309 | 2/1989 | Japan . | |
| 7854 | of 1890 | United Kingdom | 252/132 |
| 21438 | of 1892 | United Kingdom | 252/132 |
| 21414 | of 1893 | United Kingdom | 252/132 |

*Primary Examiner*—Paul Lieberman
*Assistant Examiner*—Necholus Ogden
*Attorney, Agent, or Firm*—Frost & Jacobs

[57] ABSTRACT

Soap bars which both clean and moisturize the skin are disclosed. The soap bars contain, in addition to conventional bar soap components, a mixture of petrolatum and a specifically defined emollient, preferably an hydroxylated milk glyceride.

9 Claims, No Drawings

MOISTURIZING SOAP BAR

TECHNICAL FIELD

The present invention relates to personal cleansing bar soap products, especially for use in the bath or shower, which are formulated for mildness, stability and moisturization.

BACKGROUND OF THE INVENTION

The need for mild moisturizing skin cleansing compositions is well known and is made more acute by the general aging trend of the human population, as well as the ever increasing environmental insult to which skin is subjected. The mildest currently-available skin cleansing products can, at best, produce cleansing without negatively effecting the skin condition. To achieve an improvement in skin condition, the consumer is generally forced to use a second, separate product often called a moisturizer. The use of two separate products to achieve the desired skin state is inconvenient and often unpleasant due to the greasy skin feel which results from use of many moisturizers. As a result, many persons suffer from the effects of poor skin condition, rather than use two separate products. There is clearly a need for a single product which is capable of effectively delivering both mild skin cleansing and a skin conditioning benefit. This is particularly true in the case of older people since as skin ages it becomes thin, dry, itchy, fissured, and cracked, leaving areas particularly susceptible to dryness and irritation.

Many skin cleansing products contain humectant substances which, although effective when applied topically, are ineffective when delivered to the skin from a cleansing product. These humectants are ineffective because they are very water soluble and suffer from poor skin subtantivity. Hydrophobic emollient materials are generally more substantive to the skin, but are more difficult to incorporate into an aqueous skin cleansing matrix. There are at least two sources of difficulty which are typically encountered: poor lather effects and physically unstable products.

Petrolatum is a well-known occlusive moisturizer which would be desirable to incorporate into a bar soap formulation. However, this has been difficult to accomplish as a result of the very greasy and hydrophobic properties of the material. Particle size control has, in the past, been found to be important for the effective use of petrolatum in skin cleansing products.

U.S. Pat. No. 3,829,563, Barry, et al, issued Aug. 13, 1974, discloses a liquid skin cleansing composition containing 10 to 70% petrolatum having a particle size diameter smaller than 5 microns.

U.S. Pat. No. 5,312,559, Kacher, et al, issued May 17, 1994, describes a stable, mild soap personal cleansing and moisturizing composition which contains free fatty acid soap, free fatty acid, water, and large particle size (i.e., greater than about 45 microns) petrolatum. The composition may be formulated as a bar soap.

These and similar compositions tend to be difficult to formulate since they require very specific particle size limits in order to permit formulation and use. In addition, the physical characteristics of the petrolatum tend to detract from the cosmetic-acceptability of the compositions, as the material does not spread well when applied to the skin.

It has now been found that by incorporating certain specific types of emollients, especially hydroxylated milk glycerides, into bar soap compositions, formulations containing petrolatum, which provide several unexpected benefits to both the manufacturer and the user, can be provided. Specifically, the compositions of the present invention enhance spreading of the petrolatum on skin, making them cosmetically acceptable and eliminating the need for formulations which require specific particle size distributions for the petrolatum, as are disclosed in the Kacher, et al patent, discussed above. In addition, the compositions permit the inclusion of milk glyceride materials into higher pH products without having any significant degradation of those materials. Finally, the compositions of the present invention provide improved processing in that they minimize double stamping and provide soap bars having very clean stamped edges. These benefits are obtained without the need of using any additional release agents in the formula.

Japanese Patent Application 01-45309, published Feb. 17, 1989, describes a moisturizing toilet soap which contains 5–10% skim or defatted milk.

Great Britain Patent Specification 21,414, published Sep. 30, 1893, describes a soap having excellent emollient properties which contains milk, skim milk or buttermilk. See, also, Great Britain Patent Specification 7,854, published Jun. 21, 1890, and Great Britain Patent Specification 21,438, published Feb. 27, 1892.

U.S. Pat. No. 4,704,224, Saud, issued Nov. 3, 1987, describes the use of coconut fatty acid soap together with tallow fatty acid soap in a bar soap composition to produce rich lather. An 80:20 weight ratio of tallow:coconut soap is particularly preferred.

U.S. Pat. No. 5,002,680, Schmidt, et al, issued Mar. 26, 1991, describes mild skin cleansing aerosol mouse emulsions which are taught to effectively moisturize skin. Petrolatum may be used as a moisturizer in the formulation.

A Cremerol™ HMG trade brochure (published by Amerchol Corporation, dated July, 1994) describes Cremerol™, a stable hydroxylated milk glyceride, as an excellent emollient for use in skin creams and lotions. The brochure does not describe use of the material in soap or in combination with petrolatum. Cremerol™ is taught to be equivalent to petrolatum in terms of skin moisturizing efficacy while exhibiting superior cosmetic properties. Cremerol™ is also taught to have a high spreading coefficient such that a mixture of mineral oil with Cremerol™ increases significantly the spreading coefficient of the mineral oil.

A Glucam™ trade brochure (published by Amerchol Corporation) describes a family of alkoxylated glucose derivatives as effective humectants, moisturizers and emollients which may be used in a wide variety of cosmetics, toiletries and dermatologicals, including skin lotions and bar soaps.

SUMMARY OF THE INVENTION

The present invention relates to moisturizing soap bars which comprise from about 50% to about 99% soap, from about 0.5% to about 10% petrolatum, and from about 0.1% to about 10% of an emollient selected from the group consisting of hydroxylated milk glycerides, alkoxylated glucose derivatives, lanolin, acetylated lanolin alcohols, mineral oil, isopropyl myristate, glyceryl dilaurate, hydroxylated lanolin, methyl glucose ether, and mixtures of those materials. The preferred emollients for use in the present invention are hydroxylated milk glycerides. The compositions of the present invention preferably also contain low levels of an acyl isethionate surfactant. It is also preferred that at least a portion of the soap material included in the soap bars be coconut soap. The purpose of both the isethionate and coconut soap components is to enhance the lather and the mildness of the composition.

DETAILED DESCRIPTION OF THE INVENTION

The required and the optional components of the bar soap compositions of the present invention will be discussed in detail below.

As used herein, all percentages and ratios are "by weight" unless otherwise specified.

The bar soap compositions of the present invention contain from about 50% to about 99%, preferably from about 60% to about 98%, more preferably from about 75% to about 98% of a soap material. In order to provide enhanced lather and skin mildness, it is preferred that at least about 15%, more preferably at least about 20%, and most preferably at least about 25% of this soap component be a coconut soap. It is also preferred that no more than about 50% of the total soap component be coconut soap in order to minimize any soap bar softening effects which the coconut soap may have.

The soap component of the present compositions is an alkali metal (e.g., sodium or potassium) soap or mixture of soaps of fatty acids containing from about 8 to about 24, preferably from about 10 to about 20, carbon atoms. The fatty acids used in making the soaps can be obtained from natural sources such as, for instance, plant or animal-derived glycerides (e.g., palm oil, coconut oil, babassu oil, soybean oil, castor oil, whale oil, fish oil, tallow, grease, lard, or mixtures thereof). The fatty acids can also be synthetically prepared (e.g., by oxidation of petroleum stocks by the Fischer-Tropsch process).

Alkali metal soaps can be made by direct saponification of the fats and oils or by the neutralization of the free fatty acids which are prepared in a separate manufacturing process. Particularly useful are the sodium and potassium salts of the mixtures of fatty acids derived from coconut oil and tallow, i.e., sodium and potassium tallow and coconut soaps.

The term "tallow" is used herein in connection with the fatty acid mixtures which typically have an approximate carbon chain length distribution of 2.5% $C_{14}$, 29% $C_{16}$, 23% $C_{18}$, 2% palmitoleic, 41.5% oleic, and 3% linoleic. The first three fatty acids of those listed above are saturated. Other mixtures with similar distributions, such as the fatty acids derived from various animal tallows and lard, are also included within the term "tallow". The tallow can also be hardened (i.e., hydrogenated) to convert part or all of the unsaturated fatty acid moieties to saturated fatty acid moieties.

When the terms "coconut oil" and "coconut fatty acid" are used herein, they refer to fatty acid mixtures which typically have an approximate carbon chain length distribution of 8% $C_8$, 7% $C_{10}$, 48% $C_{12}$, 17% $C_{14}$, 9% $C_{16}$, 2% $C_{18}$, 7% oleic, and 2% linoleic. The first six fatty acids listed above are saturated. Other sources having similar carbon chain length distributions, such as palm kernel oil and babassu kernel oil, are included within the terms "coconut oil" and "coconut fatty acid" as used herein.

In the compositions of the present invention, the soap component is preferably either sodium soap or a mixture of sodium and potassium soap wherein the mixture contains no more than about 25% by weight potassium soap. Also, it is preferable in such bars that the total soap component comprises (a) from about 10% to about 90% by weight of the soap component of a mixture containing soaps having from 8 to 14 carbon atoms, and (b) from about 10% to about 90% by weight of the soap component of a mixture containing soaps having from about 16 to about 20 carbon atoms.

Soaps having such preferred chain length distribution characteristics can be realized by utilizing, for example, mixtures of tallow and coconut fatty acids in tallow/coconut weight ratios varying between about 90:10 and 50:50. A mixture of soaps of tallow and coconut fatty acids in the tallow/coconut weight ratio of 80:20 is especially preferred.

The compositions of the present invention also must contain from about 0.5% to about 10%, preferably from about 1% to about 8%, and most preferably from about 1% to about 5% petrolatum, a well-known occlusive-type moisturizer. The petrolatum useful in the present invention can be any grade of light or yellow petrolatum recognized in the art as suitable for human application. The preferred material is USP Class III having a melting point between 122° and 135° F. (50° and 57° C.). Such a material is commercially available as Penreco Snow White Pet USP. Another preferred material is commercially available as Alba-White from Sonneborn. The petrolatum used in the present invention includes hydrocarbon mixtures formulated with mineral oils in combination with paraffin waxes of various melting points.

The third required component of the soap bars of the present invention is from about 0.1% to about 10%, preferably from about 0.5% to about 8%, more preferably from about 0.5% to about 5%, and most preferably from about 1% to about 3% of an emollient from a specially selected group of materials. Particularly preferred emollient materials for use in the present invention are hydroxylated milk glycerides. Milk fat is the lipid fraction of milk. It is a complex mixture of mono-, di-, and triglycerides, with over 90% of the total lipid fraction in the form of triglycerides. These triglycerides are a combination of short, medium and long chain fatty acids. The vast majority are long chain fatty acids with carbon chain lengths of 16 (palmitic acid) and 18 (stearic and oleic acids) being the most abundant. It is important that the milk glyceride materials utilized in the present invention comprise a significant percentage of unsaturated fatty acids with all of the fatty acids having an even number of carbon atoms. Although there are minor variations in the fatty acid content found in milk fat, a typical analysis is as follows.

| Fatty Acid | | Approx. Content Percent Weight |
|---|---|---|
| Saturated | | |
| Butyric | (4:0)* | 2.8 |
| Caproic | (6:0) | 2.3 |
| Caprylic | (8:0) | 1.1 |
| Capric | (10:0) | 3.0 |
| Lauric | (12:0) | 2.9 |
| Myristic | (14:0) | 8.9 |
| Palmitic | (16:0) | 24.0 |
| Stearic | (18:0) | 13.2 |
| Unsaturated | | |
| Myristoleic | (14:1) | 0.7 |
| Palmitoleic | (16:1) | 1.8 |
| Oleic | (18:1) | 29.6 |
| Linoleic | (18:2) | 2.1 |
| Linolenic | (18:3) | 0.5 |

*A shorthand designation for fatty acids is used in this table. The first number indicates carbon chain length, the second number gives the number of double bonds.

Fatty acids are found in random combination in the mixed triglycerides. Though the combinations are not infinite, there are well over 100,000 varieties found naturally. A general structure for these triglycerides can be depicted as follows:

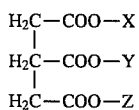

X, Y and Z can be any of the saturated or unsaturated fatty acids found in the Table, above. The average percent will dictate the level present, but does not predict the order in which it appears in the triglyceride. A triglyceride may contain a single fatty acid in all three positions (X, Y and Z), or two positions. More likely, X, Y and Z will be represented by three different acids. This milk fat is then hydroxylated such that the double bonds of the as yet unsaturated fatty acid components are saturated. This prevents the process of free radical lipid oxidation from starting, thereby preventing rancidity of the material. The hydroxylation process also destroys the lipase enzyme and reduces the water level present in the milk product to less than about 0.5%. This prevents liberation of butyric fatty acid, which causes the classic spoiled milk odor. An example of such an hydroxylated milk glyceride material is sold under the trade name Cremerol™ HMG, by Amerchol Corporation, Edison, N.J. Other emollients useful in the present invention include alkoxylated glucose derivatives, such as those sold under the trade name Glucam™ by Amerchol Corporation, lanolin, hydroxylated lanolin, acetylated lanolin alcohols, mineral oil, isopropyl myristate, glyceryl dilaurate, methyl glucose ether, and mixtures of those materials. In formulating the compositions of the present invention, the ratio by weight of emollient to petrolatum component should be from about 1:6 to about 6:1, preferably from about 1:3 to about 3:1. Preferred emollients include the hydroxylated milk glycerides and alkoxylated glucose derivatives, with hydroxylated milk glycerides being particularly preferred.

The alkoxylated glucose derivatives useful in the present invention are ethoxylated and/or propoxylated and, preferably, have the following structural formulas:

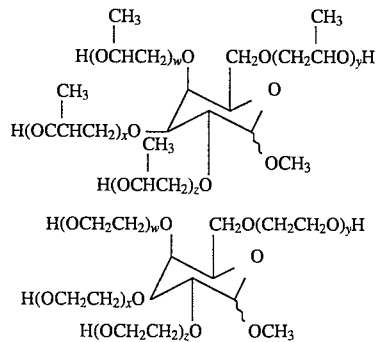

In preferred compositions, the sum w+x+y+z is from about 5 to about 40, preferably from about 10 to about 20.

Preferred compositions of the present invention additionally contain from about 0.5% to about 10% of an acyl isethionate surfactant in order to provide creamier lather and skin mildness benefits. Acyl isethionates are aliphatic higher fatty esters of an alkali metal isethionic acid salt and can be defined by the following general formula: $RCOOCH_2CH_2SO_3M$, wherein R is an aliphatic radical or a mixed aliphatic radical of a higher fatty acid or mixture thereof having from about 6 to about 20 carbon atoms, preferably from about 8 to about 18 carbon atoms, e.g., cocoyl or an approximately equivalent distribution of chain lengths, the longer chains (16 and 18) being more preferred as non-lathering, non-soil-load diluents, and medium chains ($C_{12-C14}$) being more preferred as lathering synthetic surfactants; and wherein M is an alkali metal cation such as sodium, potassium, or ammonium, or an organic amine base such as triethanolamine, tri-isopropanolamine, diethanolamine and ethanolamine. The preferred cation for the acyl isethionate material is sodium.

The soap bar compositions of the present invention may contain as optional components any of the materials conventionally found in toilet soap bars at their art-established usage levels. The toilet bars may contain from about 1% to about 25% water.

Conventional antibacterial agents can be included in the present compositions at levels of from about 0.5% to about 4% to provide users with a deodorant benefit. Typical antibacterial agents which are suitable for use herein include 3, 4-di- and 3, 4', 5-tri-bromosalicyla-anilides; 4, 4'-dichloro-3-(trifluoromethyl) carbanilide; 3, 4, 4'-trichlorocarbanilide, and mixtures of these materials. Conventional nonionic emollients (not including the required emollients, described previously) can also be included as additional skin conditioning agents in the compositions of the present invention at levels up to about 40%, preferably at levels of from about 1% to about 25%. Such materials include, for example, paraffin wax having a melting point of from about 100° F. (37° C.) to about 170° F. (77° C.), squalene, and fatty sorbitan esters (see, U.S. Pat. No. 3,988,255, Seiden, issued Oct. 26, 1976, incorporated by reference herein).

Free fatty acid such as coconut fatty acid can be added to the compositions herein to improve the volume and quality (creaminess) of the lather produced by those compositions. Preservatives may be included to enhance the shelf-stability of the compositions. Conventional perfumes, dyes and pigments can also be incorporated into compositions of the present invention at levels up to about 5%. Perfumes are preferably used at levels of from about 0.5% to about 3%, and dyes and pigments are preferably used at levels of from about 0.001% to about 0.5%.

Synthetic detergents can also be present in the compositions herein. Examples of such materials are described in U.S. Pat. No. 5,312,559, Kacher, et al, issued May 17, 1994, incorporated herein by reference. Preferred types of synthetic detergents are of the anionic or nonionic types. Examples of anionic synthetic detergents are the salts of organic sulfuric reaction products such as alkyl sulfates having the formula $$R^2OSO_3M$$

alkyl sulfonates having the formula $$R^2SO_3M$$

alkyl ether sulfates having the formula $$R^2(OC_2H_4)_xOSO_3M$$

alkyl monoglyceride sulfonates having the formula

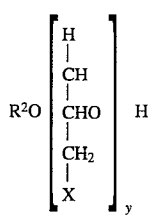

and alkyl benzene sulfonates having the formula

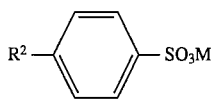

In the above formulae, $R^2$ is a straight or branched chain alkyl having from about 8 to about 24 carbon atoms; M is an alkali metal or ammonium ion; x is a number of from 1 to about 10; y is a number of from about 1 to about 4; and X is selected from the group consisting of chlorine, hydroxyl, and —$SO_3M$, at least one X in each molecule being —$SO_3M$. Examples of nonionic synthetic detergents are ethoxylated fatty alcohols (e.g., the reaction product of one mole of coconut fatty alcohol with from about 3 to 30 about moles of ethylene oxide) and fatty acid amides, such as coconut fatty acid monoethanolamide and stearic acid diethanolamide. Although it may be desirable in some instances to incorporate synthetic detergents into the compositions of the present invention, the compositions herein can be free of synthetic detergents. Synthetic detergents when present are normally employed at levels of from about 1% to about 300% by weight of the amount of soap in the compositions.

Insoluble alkaline earth metal soaps such as calcium stearate and magnesium stearate can also be incorporated into compositions of the present invention at levels up to about 30%. These materials are particularly useful in toilet bars in which synthetic detergents are present in that they tend to reduce the relatively high solubility which such bars normally have. These alkaline earth metal soaps are not included within the term "soap" as otherwise used in this specification. The term "soap" as used herein refers to the alkali metal soaps.

The soap bars of the present invention can be prepared in the conventional manner. The petrolatum and the emollient components are generally added to the base soap, frequently in the form of soap noodles, in an amalgamator. Prior to addition, the petrolatum is heated (e.g., to about 120° F. (49° C.)) in order to put it in liquid form. The emollient is also heated and liquified prior to addition to the amalgamator. However, if hydroxylated milk glyceride is used as the emollient, care must be taken so as not to heat it too high (e.g., no greater than about 40° C.) in order to avoid degradation of the material. Any optional ingredients, such as perfumes, dyes, surfactants, are also added to the amalgamator. The mixture is processed in the amalgamator and milled in the conventional manner under conventional conditions. It is then extruded (plodded) into logs for cutting and stamping into soap bars.

The soap bars of the present invention are used in a conventional manner. The skin to be cleansed is moistened with water, the soap is applied to the area to be cleaned and the area is rubbed in order to produce a lather. The lather is then rinsed off. The process may be repeated as many times as necessary to achieve the desired cleaning. When used, the soap bars of the present invention not only provide effective cleaning and are mild to the skin, but also moisturize the skin. This makes them particularly useful for use by older people, people who have a history of dry skin, and people living in very dry (low humidity) environments.

The following examples demonstrate the soap bars of the present invention and the way in which they are manufactured. These examples are given as illustration only and are not intended to be limiting of the scope of the present invention.

EXAMPLE 1

A soap bar of the present invention, having the formula given below, is made as follows.

| Part | Ingredients | % | Supplier |
|---|---|---|---|
| A | Soap Pellets (75% Tallow/25% Coconut) | 94.40 | Armour Soap Co. |
| B | Sodium Cocoyl Isethionate (80% Active) | 1.00 | Fintex (Tauranol I-78) |
| C | Petrolatum | 2.00 | Sonneborn (Alba-White) |
| D | Hydroxylated Milk Glyceride | 1.50 | Amerchol (Cremerol HMG) |
| E | TiO$_2$ | 0.35 | Whittaker-Clark Daniels |
| F | Fragrance | 0.75 | (Masking Fragrance) |
| G | Preservatives | qs | |
| | | 100.0% | |

The soap pellets and the sodium cocoyl isethionate are weighed out and added to an amalgamator. The soap pellets utilized in this example have a moisture content of about 10.5–11%. As a general rule, the soap materials utilized in the present invention have a moisture content between about 10% and about 15%, preferably between about 10.5% and about 12.5%. The petrolatum is then weighed out into a stainless steel container and liquified at 120° F. (49° C.). The liquid petrolatum is added to the ingredients already in the amalgamator with the agitator on. The hydroxylated milk glyceride is then weighed out and liquified by heating to about 40° C., with agitation. The hydroxylated milk glyceride is added to the remaining components in the amalgamator with the agitator on. Titanium dioxide, fragrance and preservative are then weighed out and added separately to the amalgamator. Components are mixed for 5 minutes, processed through a plodder and stamped into soap bars in a bar making system.

The soap bars are very easy to manufacture and process and are formed without any double stamping and with very crisp, clean bar edges. When used in a conventional manner, the soap bars are mild and provide effective cleaning and moisturizing to the skin.

EXAMPLE 2

A soap bar of the present invention, having the formula given below, is made according to the process described in Example 1.

| Part | Ingredient | % | Supplier |
|---|---|---|---|
| A | Soap Pellets (75% Tallow/25% Coconut) | 93.90 | Armour Soap Co. |
| B | Sodium Cocoyl Isethionate | 1.50 | Fintex |

-continued

| Part | Ingredient | % | Supplier |
|------|------------|------|----------|
|  | (80% active) |  | (Tauranol I-78) |
| C | Petrolatum | 2.50 | Sonneborn (Alba-White) |
| D | Methyl Gluceth-10 | 1.00 | Amerchol (Glucam E-10) |
| E | TiO$_2$ | 0.35 | Whittaker-Clark Daniels |
| F | Fragrance | 0.75 |  |
| G | Preservatives | qs |  |
|  |  | 100.0% |  |

The soap bars are very easy to manufacture and process and are formed without any double stamping and with very crisp, clean bar edges. When used in a conventional manner, the soap bars are mild and provide effective cleaning and moisturizing to the skin.

Substantially similar results are obtained when the methyl gluceth component in the above formulation is replaced, in whole or in part, with lanolin, hydroxylated tanolin, acetylated lanolin alcohol, mineral oil, isopropyl myristate, glyceryl dilaurate, methyl glucose ether, and mixtures thereof.

What is claimed is:

1. A moisturizing soap bar comprising:
   (a) from about 50% to about 99% soap;
   (b) from about 0.5% to about 10% petrolatum; and
   (c) from about 0.1% to about 10% hydroxylated milk glycerides.

2. A moisturizing soap bar according to claim 1 wherein at least about 15% of the soap component is coconut soap.

3. A moisturizing soap bar according to claim 2 which additionally contains from about 0.5% to about 10% of a surfactant selected from the group consisting of acyl isethionates, alkyl sulfates, alkyl sulfonates, alkyl ether sulfates, alkyl monoglyceride sulfonates, alkyl benzene sulfonates, ethoxylated fatty alcohols, fatty acid amides, and mixtures thereof.

4. A moisturizing soap bar according to claim 3 wherein the surfactant is an acyl isethionate.

5. A moisturizing soap bar according to claim 2 wherein at least about 20% of the soap component is coconut soap.

6. A moisturizing soap bar according to claim 5 which comprises from about 60% to about 98% of the soap component.

7. A moisturizing soap bar according to claim 6 which comprises from about 1% to about 8% of the petrolatum component.

8. A moisturizing soap bar according to claim 7 which comprises from about 0.5% to about 5% of the emollient component.

9. A moisturizing soap bar according to claim 1 which comprises:
   (a) from about 75% to about 98% soap, at least 20% of said soap being coconut soap;
   (b) from about 1% to about 5% petrolatum;
   (c) from about 0.5% to about 5% hydroxylated milk glyceride; and
   (d) from 0.5% to about 10% $C_6$–$C_{20}$ acyl isethionate.

* * * * *